US005840845A

United States Patent [19]
Smith et al.

[11] Patent Number: 5,840,845
[45] Date of Patent: *Nov. 24, 1998

[54] SENESCENT CELL DERIVED INHIBITORS OF DNA SYNTHESIS

[75] Inventors: James R. Smith, Houston, Tex.; Asao Noda, Odawara, Japan

[73] Assignee: Baylor College of Medicine, Houston, Tex.

[*] Notice: The term of this patent shall not extend beyond the expiration date of Pat. No. 5,424,400.

[21] Appl. No.: 524,218

[22] Filed: Sep. 6, 1995

Related U.S. Application Data

[63] Continuation of Ser. No. 268,439, Jun. 30, 1994, abandoned, which is a continuation of Ser. No. 160,814, Jan. 3, 1994, Pat. No. 5,424,400, which is a division of Ser. No. 970,462, Nov. 2, 1992, Pat. No. 5,302,706, which is a continuation-in-part of Ser. No. 808,523, Dec. 16, 1991, abandoned.

[51] Int. Cl.$^6$ .......................... C07K 14/00; C07K 14/475
[52] U.S. Cl. .............................. 530/350; 530/395; 514/12
[58] Field of Search ............................................... 530/350

[56] References Cited

U.S. PATENT DOCUMENTS 5,424,400   6/1995   Smith et al. .

OTHER PUBLICATIONS

Xiong, Y. et al., "D Type Cyclins Associate with Multiple Protein Kinases and the DNA Replication and Repair Factor PCNA," *Cell* 71:505–514 (1992).
Harper, J.W. et al., "The p21 Cdk–Interacting Protein Cip1 is a Potent Inhibitor of G1 Cyclin–Dependent Kinases," *Cell* 75:805–816 (1993). This protein has the same sequence as SDI–1.
El–Deiry, W.S. et al., "WAF1, A Potent Mediator of p53 Tumor Suppression," *Cell* 75:817–825 (1993).
Drescher–Lincoln, C.K. et al., "Inhibition of DNA Synthesis in Proliferating Human Diploid Fibroblasts by Fusion with Senescent Cells," *Exp. Cell Res.* 144:455–462 (1983).
Drescher–Lincoln, C.K. et al., "Inhibition of DNA Synthesis in Senescent–Proliferating Human Cybrids is Mediated by Endogenous Proteins," *Exp. Cell Res.* 153:208–217 (1984).
Lumpkin, C.K. et al.,"Existence of High Abundace Antiproliferative mRNA's in Senescent Human Diploid Fibroblasts," *Science* 232:393–395 (1986).
Maier, J.A.M. et al., "Extension of the Life–Span of Human Endothelial Cells by an Interleukin–1∝ Antisense Oligomer," *Science* 249:1570–1574 (1981).
Pereira–Smith, O.M. et al., "Genetic Analysis of Infinte Division in Human Cells: Identification of Four Complemtation Groups," *Proc Natl. Acad. Sci. (U.S.A.)*85:6042–6046 (1988).
Ning, Y. et al., "Genetic Analysis of Indefinite Division in Human Cells: Evidence for a Cell Senescence–Related Gene(s) on Human Chromosome 4," *Proc Natl. Acad. Sci. (U.S.A.)* 88:5635–5639 (1991).
Smith, J.R. et al., "Negative Growth Control in cellular Senescence,"*J. Cell Biochem Suppl.* (*13 part C*) 147 (1989).

Spiering, A.L. et al., "DNA Synthesis Inhibitors and their Possible Roles in the Senescence Phenotype," *J. Cell Biochem Suppl.* (*13 part C*) 166 (1989).
West, M.D. et al., "Replicative Senescence of Human Skin Fibroblasts Correlates with a Loss of Regulation and Overexpression of Collagenase Activity," *Exp. Cell Res.* 184:138–147 (1989).
Giordano, T. et al., "Identification of a Highly Abundant cDNA Isolated from Senescent WI–38 Cells,"*Exp. Cell Res.* 185:399–406 (1989).
Sierra, F. et al., "T–Kininogen Gene Expression is Induced during Aging," *Molec. Cell. Biol.* 9:5610–5616 (1989).
Smith, J.R., "Expression of Antiproliferartive Genes in Senescent Cells," *J.A.G.S.* 35:804 (1987).
Smith, J.R., "A Hypothesis for in vitro Cellular Senescence Based on the Population Dynamics of Human Diploid Fibroblasts and Somatic Cell Hybrids," In: *Monographs in Developmental Biology;* Sauer, H.W. (Ed.), S. Karger, New York, N.Y.*17*:193–207 (1984).
Smith, J.R. et al., "Further Studies on the Genetic and Biochemical Basis of Cellular Senescence," *Exper. Gerontol.* 24:377–381 (1989).
Spiering, A.L. et al., "A Potent DNA Synthesis Inhibitor Expressed by the Immortal Cell Line SUSM–1," *Exper.Cell Res.* 179:159–167 (1988).
Pereira–Smith, O.M. et al., "Senescent and Quiescent Cell Inhibitors of DNA Synthesis Membrane–Associated Proteins," *Exper. cell Res.160*:297–306 1985;.
Spiering, A.L. et al., "Correlation between Complementation Group for Immortality and DNA Synthesis Inhibitors," *Exper. Cell Res.* 195:541–545 (1991).
Kleinsek, D.A., "Selection of mRNAs Expressed During Cellular Senescence In Vitro," *Age* 12:55–60 (1989).
Pereira–Smith, O.M. et al., "Negative Growth Control in Cellular Senescence," *J Cell. Biochem.* (Suppl 0 (12 part A) 193 (1988).
Kleinsek, D.A. et al., "Isolation of cDNA Sequences Specifics to Senescent Human Diploid Fibroblast Cells In Vitro", *Age 10*:125 (1987).
Murano, S. et al., "Diverse Gene Sequences Are Overexpressed in Werner Syndrome Fibroblasts Undergoing Premature Replicative Senescence," *Molec. Cell. Biol.* 11:3905–3914 (Aug. 1991); and.
Takebe, Y. et al., "SR∝ Promoter: An Efficient and Versatile Mammalian cDNA Expression System Composed of the Simian Virus 40 Early Promoter and the R–U5 Segment of Human T–Cell Leukemia Virus Type 1 Long Terminal Repeat," *Mol. Cell. Biol.* 8:466–472 (1988).

*Primary Examiner*—Paula K. Hutzell
*Assistant Examiner*—Stephen Gucker
*Attorney, Agent, or Firm*—Gerard P. Norton; Rogers & Wells LLP

[57] ABSTRACT

An expression vector cDNA library derived from senescent cells has been used to isolate cDNA clones that encode inhibitors of DNA synthesis. Such inhibitors play a role in cellular senescence and aging. Antisense nucleic acids reduce the inhibition of DNA synthesis.

1 Claim, 9 Drawing Sheets

```
  1:  cct gcc gaa gtc agt tcc ttg tgg agc cgg agc tgg gcg cgg att

46:  cgc cga ggc acc gag gca ctc aga gga ggc gcc atg tca gaa ccg
                                                    M   S   E   P 91:  gct ggg gat gtc cgt cag aac cca tgc ggc agc aag gcc tgc cgc
  1:   A   G   D   V   R   Q   N   P   C   G   S   K   A   C   R 136:  cgc ctc ttc ggc cca gtg gac agc gag cag ctg agc cgc gac tgt
  1:   R   L   F   G   P   V   D   S   E   Q   L   S   R   D   C 181:  gat gcg cta atg gcg ggc tgc atc cag gag gcc cgt gag cga tgg
  1:   D   A   L   M   A   G   C   I   Q   E   A   R   E   R   W 226:  aac ttc gac ttt gtc acc gag aca cca ctg gag ggt gac ttc gcc
  1:   N   F   D   F   V   T   E   T   P   L   E   G   D   F   A 271:  tgg gag cgt gtg cgg ggc ctt ggc ctg ccc aag ctc tac ctt ccc
  1:   W   E   R   V   R   G   L   G   L   P   K   L   Y   L   P 316:  acg ggg ccc cgg cga ggc cgg gat gag ttg gga gga ggc agg cgg
  1:   T   G   P   R   R   G   R   D   E   L   G   G   G   R   R 361:  cct ggc acc tca cct gct ctg ctg cag ggg aca gca gag gaa gac
  1:   P   G   T   S   P   A   L   L   Q   G   T   A   E   E   D 406:  cat gtg gac ctg tca ctg tct tgt acc ctt gtg cct cgc tca ggg
  1:   H   V   D   L   S   L   S   C   T   L   V   P   R   S   G
```

FIG.5A

451: gag cag gct gaa ggg tcc cca ggt gga cct gga gac tct cag ggt
  1:  E   Q   A   E   G   S   P   G   G   P   G   D   S   Q   G 496: cga aaa cgg cgg cag acc agc atg aca gat ttc tac cac tcc aaa
  1:  R   K   R   R   Q   T   S   M   T   D   F   Y   H   S   K 541: cgc cgg ctg atc ttc tcc aag agg aag ccc taa tcc gcc cac agg
  1:  R   R   L   I   F   S   K   R   K   P 586: aag cct gca gtc ctg gaa gcg cga ggg cct caa agg ccc gct cta 631: cat ctt ctg cct tag tct cag ttt gtg tgt ctt aat tat tat ttg 676: tgt ttt aat tta aac acc tcc tca tgt aca tac cct ggc cgc ccc 721: ctg ccc ccc agc ctc tgg cat tag aat tat tta aac aaa aac tag 766: gcg gtt gaa tga gag gtt cct aag agt gct ggg cat ttt tat ttt 811: atg aaa tac tat tta aag cct cct cat ccc gtg ttc tcc ttt tcc 856: tct ctc ccg gag gtt ggg tgg gcc ggc ttc atg cca gct act tcc 901: tcc tcc cca ctt gtc cgc tgg gtg gta ccc tct gga ggg gtg tgg 946: ctc ctt ccc atc gct gtc aca ggc ggt tat gaa att cac ccc ctt 991: tcc tgg aca ctc aga cct gaa ttc ttt ttc att tga gaa gta aac

FIG.5B

```
1036:  aga tgg cac ttt gaa ggg gcc tca ccg agt ggg ggc atc atc aaa

1081:  aac ttt gga gtc ccc tca cct cct cta agg ttg ggc agg gtg acc

1126:  ctg aag tga gca cag cct agg gct gag ctg ggg acc tgg tac cct

1171:  cct ggc tct tga tac ccc cct ctg tct tgt gaa ggc agg ggg aag

1216:  gtg ggg tcc tgg agc aga cca ccc cgc ctg ccc tca tgg ccc ctc

1261:  tga cct gca ctg ggg agc ccg tct cag tgt tga gcc ttt tcc ctc

1306:  ttt ggc tcc cct gta cct ttt gag gag ccc cag cta ccc ttc ttc

1351:  tcc agc tgg gct ctg caa ttc ccc tct gct gct gtc cct ccc cct

1396:  tgt cct ttc cct tca gta ccc tct cag ctc cag gtg gct ctg agg

1441:  tgc ctg tcc cac ccc cac ccc cag ctc aat gga ctg aag gga gaa

1486:  ggg aca cac aag aag aag ggc acc cta gtt cta cct cag gca gct

1531:  caa gca gcg acc gcc ccc tcc tct agc tgt ggg ggt gag ggt ccc

1576:  atg tgg tgg cac agg ccc cct tga gtg ggg tta tct ctg tgt tag

1621:  ggg tat atg atg ggg gag tag atc ttt cta gga ggg aga cac tgg

1666:  ccc ctc aaa tcg tcc agc gac ctt cct cat cca ccc cat ccc tcc
```

FIG.5C

1711: cca gtt cat tgc act ttg att agc agc gga aca agg agt cag aca

1756: ttt taa gat ggt ggc agt aga ggc tat gga cag ggc atg cca cgt

1801: ggg ctc ata tgg ggc tgg gag tag ttg tct ttc ctg gca cta acg

1846: ttg agc ccc tgg agg cac tga agt gct tag tgt act tgg agt att

1891: ggg gtc tga ccc caa aca cct tcc agc tcc tgt aac ata ctg gcc

1936: tgg act gtt ttc tct cgg ctc ccc atg tgt cct ggt tcc cgt ttc

1981: tcc acc tag act gta aac ctc tcg agg gca ggg acc aca ccc tgt

2026: act gtt ctg tgt ctt tca cag ctc ctc cca caa tgc tga tat aca

2071: gca ggt gct caa taa acg att ctt agt gaa aaa aaa

FIG.5D

SENESCENT CELL DERIVED INHIBITORS OF DNA SYNTHESIS

CROSS-REFERENCE TO RELATED APPLICATIONS

This is a continuation Ser. No. 08/268,439, filed Jun. 30, 1994 now abandoned, which is a continuation of Ser. No. 08/160,814, filed Jan. 3, 1994, now U.S. Pat. No. 5,424,400, issued Jun. 13, 1995, which is a divisional of Ser. No. 07/970,462, filed Nov. 2, 1992, now U.S. Pat. No. 5,302,706, issued Apr. 12, 1994, which is a continuation-in-part of U.S. Ser. No. 07/808,523, filed Dec. 16, 1991, now abandoned, all incorporated herein by reference.

FIELD OF THE INVENTION

The present invention is in the field of recombinant DNA technology. This invention is directed to a gene sequence and a protein that effects the ability of cells to become senescent. This invention was supported with Government funds. The Government has certain rights in this invention.

BACKGROUND OF THE INVENTION

Normal human diploid cells have a finite potential for proliferative growth (Hayflick, L. et al., *Exp. Cell Res.* 25:585 (1961); Hayflick, L., *Exp. Cell Res.* 37:614 (1965)). Indeed, under controlled conditions in vitro cultured human cells can maximally proliferate only to about 80 cumulative population doublings. The proliferative potential of such cells has been found to be a function of the number of cumulative population doublings which the cell has undergone (Hayflick, L. et al., *Exp. Cell Res.* 25:585 (1961); Hayflick, L. et al., *Exp. Cell Res.* 37:614 (1985)). This potential is also inversely proportional to the in vivo age of the cell donor (Martin, G. M. et al., *Lab. Invest.* 23:86 (1979); Goldstein, S. et al., *Proc. Natl. Acad. Sci. (U.S.A.)* 64:155 (1969); Schneider, E. L. *Proc. Natl. Acad. Sci. (U.S.A.)* 74:3584 (1976); LeGuilty, Y. et al., *Gereontologia* 19:303 (1973)).

Cells that have exhausted their potential for proliferative growth are said to have undergone "senescence." Cellular senescence in vitro is exhibited by morphological changes and is accompanied by the failure of a cell to respond to exogenous growth factors. Cellular senescence, thus, represents a loss of the proliferative potential of the cell. Although a variety of theories have been proposed to explain the phenomenon of cellular senescence in vitro, experimental evidence suggests that the age-dependent loss of proliferative potential may be the function of a genetic program (Orgel, L. E., *Proc. Natl. Acad. Sci. (U.S.A.)* 49:517 (1963); De Mars. R. et al., *Human Genet.* 16:87 (1972); M. Buchwald, *Mutat. Res.* 44:401 (1977); Martin, G. M. et al., *Amer. J. Pathol.* 74:137 (1974); Smith, J. R. et al., *Mech. Age. Dev.* 13:387 (1980); Kirkwood, T. B. L. et al., *Theor. Biol.* 53:481 (1975).

Cell fusion studies with human fibroblasts in vitro have demonstrated that the quiescent phenotype of cellular senescence is dominant over the proliferative phenotype (Pereira-Smith, O. M. et al., *Somat. Cell Genet.* 8:731 (1982); Norwood, T. H. et al., *Proc. Natl. Acad. Sci. (U.S.A.)* 71:223 (1974); Stein, G. H. et al., *Exp. Cell Res.* 130:155 (1979)).

Insight into the phenomenon of senescence has been gained from studies in which senescent and young (i.e. non-senescent) cells have been fused to form heterodikaryons. In order to induce senescence in the "young" nucleus of the heterodikaryon (as determined by an inhibition in the synthesis of DNA), protein synthesis must occur in the senescent cell prior to fusion (Burmer, G. C. et al., *J. Cell. Biol.* 94:187 (1982); Drescher-Lincoln, C. K. et al., *Exp. Cell Res.* 144:455 (1983); Burner, G. C. et al., *Exp. Cell Res.* 145:708 (1983); Drescher-Lincoln, C. K. et al., *Exp. Cell Res.* 153:208 (1984).

Likewise, microinjection of senescent fibroblast mRNA into young fibroblasts has been found to inhibit both the ability of the young cells to synthesize DNA (Lumpkin, C. K. et al., *Science* 232:393 (1986)) and the ability of the cells to enter into the S (stationary) phase of the cell cycle (Lumpkin, C. K. et al., *Exp. Cell Res.* 160:544 (1985)). Researchers have identified unique mRNAs that are amplified in senescent cells in viro (West, M. D. et al., *Exp. Cell Res.* 185:138 (1989); Giordano, T. et al., *Exp. Cell Res.* 185:399 (1989)).

The human diploid endothelial cell presents an alternative cell type for the study of cellular senescence because such cells mimic cellular senescence in vitro (Maciag, T. et al., *J. Cell. Biol.* 91:420 (1981); Gordon, P. B. et al., *In vitro* 19:661 (1983); Johnson, A. et al., *Mech Age. Dev.* 18:1 (1982); Thornton, S. C. et al., *Science* 222:623 (1983); Van Hinsbergh, V. W. M. et al., *Eur. J. Cell Biol.* 42:101 (1986); Nichols, W. W. et al., *J. Cell. Physiol.* 132:453 (1987)).

In addition, the human endothelial cell is capable of expressing a variety of functional and reversible phenotypes. The endothelial cell exhibits several quiescent and non-terminal differentiation phenotypes (Folkman, J. et al., *Nature* 288:551 (1980); Maciag, T. et al., *J. Cell Biol.* 94:511 (1982); Madri. J. A. et al., *J. Cell Biol.* 97:153 (1983); Montesano, R., *J. Cell Biol.* 99:1706 (1984); Montesano, R. et al., *J. Cell Physiol.* 34:460 (1988)).

It has been suggested that the pathway of human cell differentiation in vitro involves the induction of cellular quiescence mediated by cytokines that inhibit growth factor-induced endothelial cell proliferation in vitro (Jay, M. et al., *Science* 228:882 (1985); Madri, J. A. et al., *In Vitro* 23:387 (1987); Kubota, Y. et al., *J. Cell Biol.* 107:1589 (1988); Ingber, D. E. et al., *J. Cell Biol.* 107:317 (1989)).

Inhibitors of endothelial cell proliferation also function as regulators of immediate-early transcription events induced during the endothelial cell differentiation in vitro, which involves formation of the capillary-like, tubular endothelial cell phenotype (Maciag, T., In: *Imp. Adv. Oncol.* (De Vita, V. T. et al., eds., J. B. Lippincott, Philadelphia, 42 (1990); Goldgaber, D. et al., *Proc. Natl. Acad. Sci. (U.S.A.)* 86:7606 (1990); Hla, T. et al., *Biochem. Biophys. Res. Commun.* 167:637 (1990)). The inhibitors of cell proliferation that include:

1. Interleukin-1a (IL-1a) (Montesano, R. et al., *J. Cell Biol.* 99:1706 (1984); Montesano, R. et al., *J. Cell Physiol.* 122:424 (1985); Maciag, T. et al. (*Science* 249:1570–1574 (1990);
2. Tumor necrosis factor (Frater-Schroder, M. et al., *Proc. Natl. Acad. Sci. (U.S.A.)* 84:5277 (1987); Sato, N. et al., *J. Natl. Cancer Inst.* 76:1113 (1986); Pber, J. P., *Amer. J. Pathol.* 133:426 (1988); Shimada, Y. et al., *J. Cell Physiol.* 142:31 (1990);
3. Transforming growth factor-β (Baird, A. et al., *Biochem. Biophys. Res. Commun.* 138:476 (1986); Mullew, G. et al., *Proc. Natl. Acad. Sci. (U.S.A.)* 84:5600 (1987); Mairi, J. A. et al., *J. Cell Biol.* 106:1375 (1988));
4. Gamma-interferon (Friesel, R. et al., *J. Cell Biol.* 104:689 (1987); Tsuruoka, N. et al., *Biochem. Biophys. Res. Commun.* 155:249 (1988)) and 5. The tumor promoter, phorbol myristic acid (PMA) (Montesano, R. et al., *Cell* 42:469 (1985); Doctrow, S. R. et al., *J. Cell Biol.* 104:679 (1987); Montesano, R. et al., *J. Cell. Physiol.* 130:284 (1987); Hoshi, H. et al., *FASAB J.* 2:2797 (1988)).

The prospect of reversing senescence and restoring the proliferative potential of cells has implications in many fields of endeavor. Many of the diseases of old age are associated with the loss of this potential. Also the tragic disease, progeria, which is characterized by accelerated aging is associated with the loss of proliferative potential of cells. Restoration of this ability would have far-reaching implications for the treatment of this disease, of other age-related disorders, and, of aging per se.

In addition, the restoration of proliferative potential of cultured cells has uses in medicine and in the pharmaceutical industry. The ability to immortalize nontransformed cells can be used to generate an endless supply of certain tissues and also of cellular products.

The significance of cellular senescence has accordingly been appreciated for several years (Smith, J. R., Cellular Ageing, In: *Monographs in Developmental Biology;* Sauer, H. W. (Ed.), S. Karger, New York, N.Y. 17:193–208 (1984); Smith, J. R. et al. *Exper. Gerontol.* 24:377–381 (1989), herein incorporated by reference). Researchers have attempted to clone genes relevant to cellular senescence. A correlation between the existence of an inhibitor of DNA synthesis and the phenomenon of cellular senescence has been recognized (Spiering, A. I. et al., *Exper. Cell Res.* 179:159–167 (1988); Pereira-Smith, O. M. et al., *Exper. Cell Res.* 160:297–306 (1985); Drescher-Lincoln, C. K. et al., *Exper. Cell Res.* 153:208–217 (1984); Drescher-Lincoln, C. K. et al., *Exper. Cell Res.* 144:455–462 (1983)). Moreover, the relative abundance of certain senescence-associated RNA molecules has been identified (Lumpkin, C. K. et al., *Science* 232:393–395 (1986)).

Several laboratories have used the "subtraction-differential" screening method to identify cDNA molecules derived from RNA species that are preferentially present in senescent cell (Kleinsek, D. A. *Age* 12:55–60 (1989); Giordano, T. et. al., *Exper. Cell. Res.* 185:399–406 (1989); Sierra, F. et al., *Molec. Cell. Biol.* 9:5610–5616 (1989); Pereira-Smith, O. M. et al., J. Cell. Biochem. (Suppl 0 (12 part A)) 193 (1988); Kleinsek, D. A., Smith J. R., *Age* 10:125 (1987)).

In one method, termed "subtraction-differential" screening, a pool of cDNA molecules is created from senescent cells, and then hybridized to cDNA or RNA of growing cells in order to "subtract out" those cDNA molecules that are complementary to nucleic acid molecules present in growing cells. Although useful for certain purposes, the "subtraction-differential" method suffers from the fact that it is not possible to determine whether a senescence-associated cDNA molecule is associated with the cause of senescence, or is produced as a result of senescence. Indeed, many of the sequences identified in this manner have been found to encode proteins of the extra-cellular matrix. Changes in the expression of such proteins would be unlikely to cause senescence.

SUMMARY OF THE INVENTION

The present invention concerns, in part, the observation that normal human cells exhibit a limited replicative potential in vitro and become senescent after a certain number of divisions. As the cells become senescent, they show several morphological and biochemical changes, such as enlargement of cell size, changes of extracellular matrix components, unresponsiveness to mitogen stimulation and failure to express growth regulated genes.

The present invention identifies an inhibitor of DNA synthesis that is produced in senescent cells. This inhibitor plays a crucial role in the expression of the senescent phenotype. The gene coding for the inhibitor was identified by incorporating a senescent cell cDNA library into a mammalian expression vector. The cDNA library was then transfected into young, cycling cells to identify those library members that suppressed the initiation of DNA synthesis.

Efficient DEAE dextran-mediated transfection enabled the isolation of putative senescent cell derived inhibitor (SDI) sequences in three distinct cDNA clones. The expression of one (SDI-1) increased 20 fold at cellular senescence, whereas that of the others (SDI-2 and SDI-3) remained constant.

In summary, the present invention achieves the cloning of an inhibitor of DNA synthesis using a functional assay. This method may be applied to clone other genes involved in negative regulation of the cell cycle, such as tissue specific differentiation and tumor suppression genes. Using this method, three inhibitor sequences have been cloned. One of these sequences (SDI-1) appears to be closely related to cellular senescence.

In detail, the invention provides a nucleic acid molecule that encodes a protein capable of inhibiting DNA synthesis in a recipient cell.

The invention particularly concerns the embodiment wherein the nucleic acid molecule is DNA, and is incorporated into a DNA plasmid (such as pcDSRαΔ).

The invention also concerns the embodiments wherein the above stated nucleic acid molecule is SDI-1, and wherein it has the sequence shown in FIG. 5 <SEQ ID 1>.

The invention also includes the embodiment wherein the nucleic acid molecule is RNA.

The invention also concerns a nucleic acid molecule (either DNA or RNA) having a sequence complementary to such RNA molecule, and a length sufficient to permit the molecules to hybridize to one another under physiological conditions.

The invention also provides a method for inhibiting DNA synthesis in a human cell which comprises providing to the cell an effective amount of the above-stated nucleic acid molecule that encodes a protein capable of inhibiting DNA synthesis in a recipient cell (and especially wherein the cell is a tumor cell, or a cell in in vitro culture.

The invention also provides a method for depressing an inhibition of DNA synthesis in a quiescent or senescent human cell which comprises providing to the cell an effective amount of a nucleic acid molecule (either DNA or RNA) having a sequence complementary to an RNA molecule that encodes a protein capable of inhibiting DNA synthesis in a recipient cell, and having a length sufficient to permit the molecules to hybridize to one another under physiological conditions. Especially contemplated is the embodiment wherein the cell is a skin cell or a cell present in wound or burn tissue. The invention further contemplates the use of the agents of the present invention in tissue other than skin, such as lymphocytes, vascular tissue (such as arteries, arterioles, capillaries, veins, etc.), liver, kidney, heart and other muscle, bone, spleen, etc.

BRIEF DESCRIPTION OF THE FIGURES

FIGS. 5A–5D provide the nucleotide (SEQ ID NO: 1) and amino acid (SEQ ID NO: 2) sequences of SDI-1 cDNA.

DETAILED DESCRIPTION OF THE INVENTION

Cellular Senescence

Figure 1:
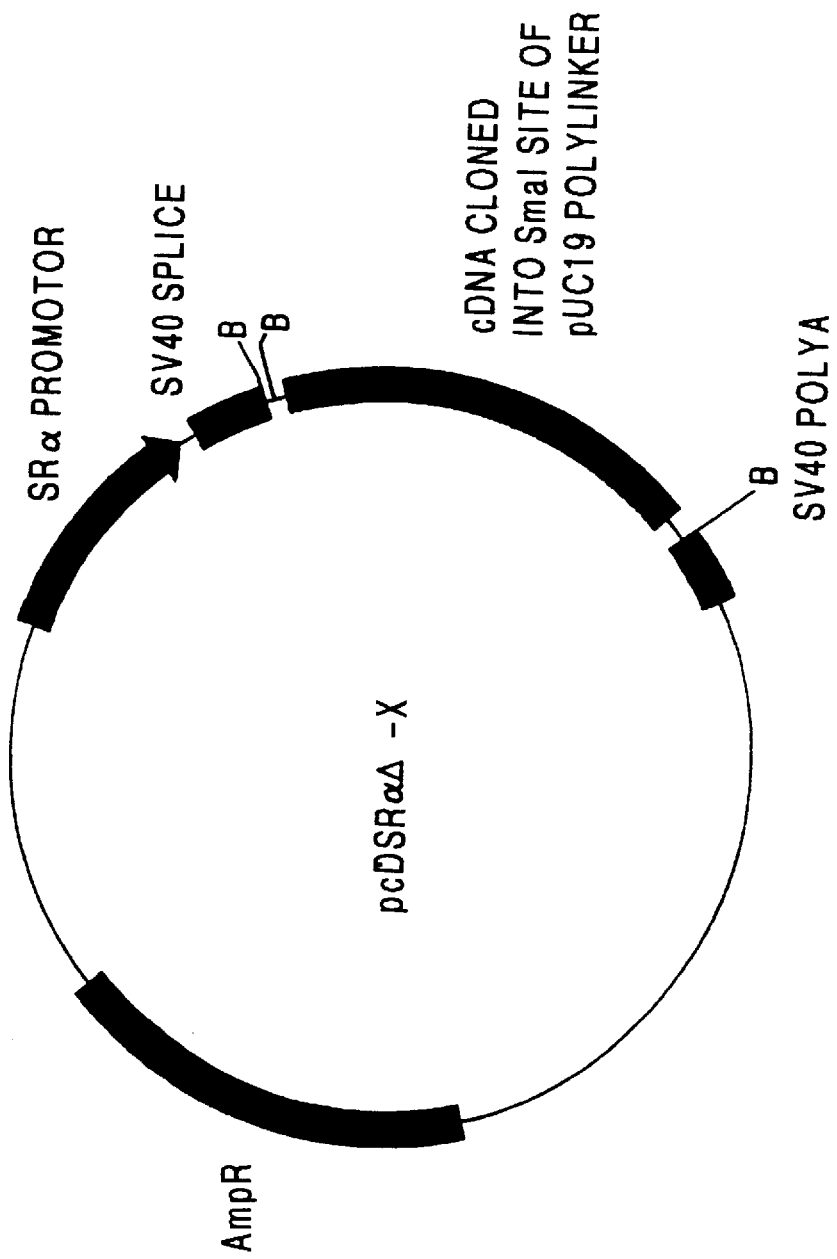
FIG. 1 shows the structure of the cDNA cloning and expression vector, pcDSRαΔ (B represents BamHI site).

Replicative senescence of normal human diploid fibroblasts in culture is a well established and widely accepted model for cellular aging (Hayflick, L., *Exp. Cell Res.* 37:611–636 (1965); Norwood, T. H., and Smith, J. R., In: *Handbook of the Biology of Aging* (2nd ed.) C. E. Finch and E. L. Schneider, eds. Van Nostrand, New York pp. 291–311 (1985); Goldstein, S., *Science* 249:1129–1133 (1990)). After a limited number of population doublings, as cells become senescent, they lose the capability to divide and display a large and flattened morphology. The causative mechanisms underlying this phenomenon are not yet understood, despite the many observations that characterize senescent cells at the biochemical and molecular levels.

One- and two-dimensional protein gel analyses have revealed that there are few senescent cell-specific marker proteins (Lincoln, D. W. et al., *Exp. Cell Res.* 154:136–146 (1984); Wang, E., *J. Cell Biol.* 100:545–551 (1985); Scottie, J. et al., *J. Cell Physiol.* 131:210–217 (1987); Bayreuther, K. et al., *Proc. Natl. Acad. Sci. USA.* 85:5112–5116 (1988)). Antigenic determinants that specify senescent cells have been found on the plasma membrane (Porter, M. B. et al., *J. Cell Physiol.* 142:425–433 (1990)). Components of extracellular matrix, such as fibronectin and collagenase, have been found to be over-expressed in senescent cells (West, M. D. et al., *Exp. Cell Res.* 184:138–147 (1989); Kumazaki, T. et al., *Exp. Cell Res.* 195:13–19 (1991)). However, the relevance of these observations to cellular senescence is not clear.

Recently, changes is the expression of several growth regulated genes have been identified. Expression of c-fos cdc2, cyclin A and B have been found to be impaired in senescent cells (Seshadri, T., and Campisi, J., *Science* 247:205–209 (1990)). Similarly, senescent cells evidence an inability to phosphorylate the retinoblastoma protein (Stein, G. H. et al., *Science* 249:666–669 (1990)). These observations could potentially explain the inability of the cells to enter S phase, since they are all deteriorative changes of growth promoting gene expression, however, it is not clear whether they are the cause or result of senescence.

One additional change in gene expression that could have a causal role in senescence is the inhibitor(s) of DNA synthesis produced by senescent but not young fibroblasts (see, Spiering, A. I. et al., *Exper. Cell Res.* 195:541–545 (1991). Evidence for the existence of the inhibitor(s) was first obtained from heterokaryon experiments in which senescent cells inhibited initiation of DNA synthesis in young nuclei within the heterokaryon (Norwood, T. H., et al., *Proc. Natl. Acad. Sci. USA*. 71:2231–2234 (1974); Pereira-Smith, O. M., and Smith, J. R., *Somat. Cell Genet.* 8:731–732 (1982)). Studies with cybrids involving senescent cytoplasts and whole young cells lent further support for the presence of a surface membrane associated protein inhibitor of DNA synthesis in senescent cells (Dresher-Lincoln, C. K., and Smith, J. R., *Exp. Cell Res.* 153:208–217 (1984)). This was directly demonstrated when surface membrane enriched preparations from senescent cells or proteins extracted from the membranes were found to inhibit DNA synthesis when added to the culture medium of young cells (Pereira-Smith, O. M. et al., Exp. Cell Res. 160:297–306 (1985); Stein, G. H., and Atkins, L., *Proc. Natl. Acad. Sci. USA*. 83:9030–9034 (1986)). Purification of that inhibitor by biochemical methods has been unsuccessful to date. However, in microinjection experiments, the presence of a high abundance of DNA synthesis inhibitory messenger RNA has been demonstrated (Lumpkin, C. K. et al., *Science* 232:393–395 (1986)).

In order to attempt to clone the gene(s) coding for the DNA synthesis inhibitor(s), a functional screening procedure was employed. This method led to the isolation and identification of three cDNA species that exhibit DNA synthesis inhibitory activity when introduced into young cycling cells. These molecules are referred to herein as "senescent cell derived inhibitors" ("SDI").

II. The Cloning of Inhibitors of Cellular Senescence

In the practice of the present invention, an efficient method for the molecular cloning of the DNA synthesis inhibitory sequences present in senescent human diploid fibroblasts is preferably employed. As is often the case when attempting to clone biologically important genes, it may not be possible to purify a desired gene responsible for cellular senescence, even though the activity of its products could be readily detected.

One method that might be envisioned for identifying such a gene sequence would be to employ a differential or subtractive screening of senescent cell derived cDNA library. This method has been used to identify cDNA molecules that are overexpressed in cells from Werner Syndrome patients (Murano, S. et al., *Molec. Cell. Biol.* 11:3905–3914 (August 1991)). Werner Syndrome is a rare inherited disorder. It is characterized by premature aging. The relevance of Werner Syndrome to natural aging is unknown.

Unfortunately, such screenings would identify a number of genes that, although important for the characterization of senescent cells, would not be primarily responsible for senescence. Furthermore, technical limitations in cloning full-length cDNA make it difficult to determine the function of genes cloned by these methods. For these reasons, such differential methods are nether generally suitable, or the most desirable method of identifying senescence-related gene sequences.

In contrast, expression screening provides a preferred method for identifying and isolating such senescence-related gene sequences. In such a screening method, the cDNA is cloned directly into a vector that is capable of expressing the cloned gene in a recipient cell. The recipient cells can thus be directly screened for any inhibition in DNA synthesis.

In expression screening, the most important step is the synthesis of cDNAs. Enzymes should be carefully chosen to be free of impurities. The cDNA synthesis is preferably repeated several times to ensure that satisfactory results (i.e faithful reverse transcription, and full length transcript size) will be obtained. Finally, the cDNA products are preferably size fractionated to eliminate fragmented and prematurely terminated cDNA products. Double stranded cDNA products are then preferably divided into fractions based on size, i.e., 0.5–2.0, 2.0–4.5, and 4.5–10 kb fractions. The 2–4.5 kb cDNA fraction was used to make the cDNA library on the assumption that many membrane associated proteins have a relatively high molecular weight. The cDNAs are inserted into a suitable expression vector, preferably pcDSRαΔ, in which the inserted sequences can be transcribed at high levels in young cells.

The most preferred transfection procedure is DEAE dextran-mediated transfection, carrier out under conditions that allowed for transient expression in a high percentage of young cycling cells. Since the transfection frequencies could vary from experiment to experiment, the cDNA pool plasmids were transfected along with a marker plasmid, such as pCMVβ (encoding β-galactosidase), and the labelling index was assayed in only β-galactosidase positive cells. Generally, co-expression of transfected genes is quite high, since transfection competent cells will accept multiple plasmids. This simple co-transfection method enabled the evaluation of DNA synthesis in cells expressing exogenous DNA.

The amount of plasmid to be co-transfected was determined from pilot experiments. When the correlation between the transfection frequency and the amount of plasmid added is examined using a marker plasmid, maximum efficiency is obtained at a range of 100–500 ng of plasmid. Taking into account this result, the cDNA library is preferably divided into small pools in which every pool contained five independent plasmid clones. Then the co-transfection is carried out with approximately 100 ng of pCMVβ and approximately 400 ng of cDNA plasmid. These parameters were found to maximize the co-expression of cDNA in β-galactosidase positive cells without decreasing the transfection frequency of the marker plasmid.

Figure 2A:
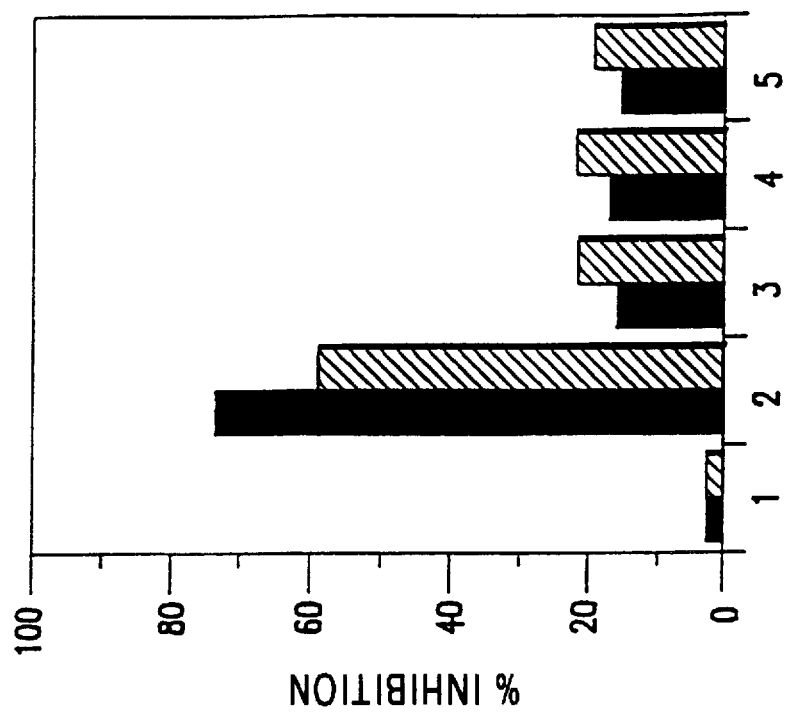
FIGS. 2A–2C identify cDNA clones inhibitory to young cell DNA synthesis. The three different bars represent independent transfection experiments, * indicates not done, a negative number indicates labelling indices higher than the controls.
Figure 2B:
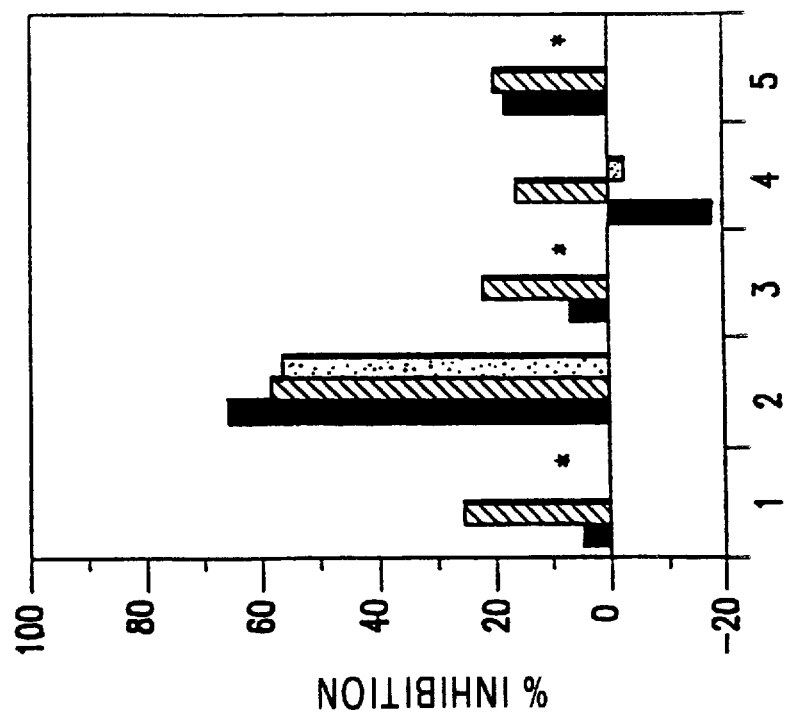
Figure 2C:
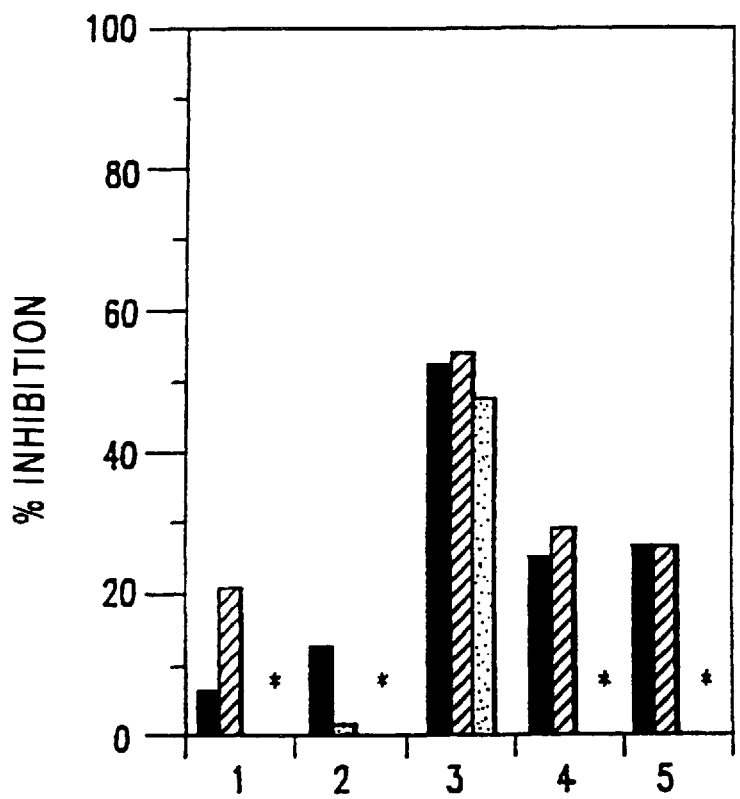

After the second round of screening, single plasmids which showed strong inhibition of DNA synthesis can be successfully isolated from the pool that tested positive during the first round screenings FIGS. 2A–2C. In FIGS. 2A–2C, cDNA pools which showed positive in the first round screenings were divided into individual plasmid, and transfected again. For every cDNA pool (A, B and C), plasmid No. 1 to 5 represents the result of each single plasmid transfection. In pool B, No. 1 plasmid was found to be only the empty vector. The inhibitory activities of the plasmids are preferably further confirmed by nuclear microinjection experiments. Such experiments provide more direct evidence that the isolated plasmids contain sequences capable of inhibiting DNA synthesis.

III. The Molecules of the Present Invention and Their Uses

The present invention contemplates the use of any of a variety of chemical agents to either inhibit or enable DNA synthesis. Such agents may be: (1) an oligonucleotide, (2) a nucleic acid binding protein, or (3) a compound whose structure mimics that of either an oligonucleotide or a nucleic acid binding molecule (i.e. a "peptidomimetic" agent).

The agents of the present invention are capable of either inducing the inhibition of DNA synthesis in active cells, or suppressing such inhibition in senescent or quiescent cells, they may be used for a wide range of therapies and applications.

Thus, in one embodiment, the present invention provides a means of isolating cDNA molecules, in functional (i.e. expressible) form, that are capable of inhibiting DNA synthesis in recipient cells. Such "SDI" nucleic acid molecules, as well as the proteins they encode, and their peptidomimetic analogs, have use in inducing a senescent or quiescent state in a recipient cell. Such induction is desirable in the treatment of progeria (Badame, A. J. Arch. Dermatol. 125:540 (1989); Hamer, L. et al., Orthoped. 11:763 (1988); Martin, G. M., Natl. Canc. Inst. Monogr. 60:241 (1982)); age-related disorder (Martin, G. M. Genome 31:390 (1989); Roe, D. A., Clin. Geriatr. Med. 6:319 (1990); Mooradian, A. D., J. Amer. Geriat. Soc. 36:831 (1988); Alpert, J. S., Amer. J. Cardiol. 65:23j (1990)); Alzheimer's disease (Terry, R. D., Monogr. Pathol. 32:41 (1990); Costall, B. et al., Pharmacopsychiatry 23:85 (1990)); asthenia and cachexia (Verdery, R. B., Geriatrics 45:26 (1990)), or diseases or conditions in which rapid cellular proliferation is undesirable. In this respect, the agents of the present invention can be used therapeutically to suppress the rapid proliferation of tumor or tumorigenic cells. Thus, the present invention provide a therapy for treating cancer.

The sequence of the SDI nucleic acid molecules permits one to ascribe and identify protein molecules that can be used to suppress the inhibition of DNA synthesis associated with quiescence and senescence. The amino acid sequence of such molecules can be readily derived from the known relationship between the nucleotide sequence of a nucleic acid molecule, and the amino acid sequence of the protein it encodes. The present invention includes the protein and polypeptide molecules that would be synthesisized through the transcription and translation of the disclosed SDI nucleic acid molecules.

An additional class of molecules that is contemplated by the present invention comprises proteins or other molecules (i.e peptidomimetic analogs) that mimic the function of the proteins expressed from the SDI sequences.

These and other analogs can be readily identified by, for example, exploiting the capacity of the agents of the present invention to induce or to derepress DNA synthesis may be used to identify agents capable of reversing these processes. Thus, for example, one may incubate cells in the presence of both an SDI oligonucleotide and a suspected antagonist compound. The cells would be monitored in order to determine whether the compound is able to impair the ability of the SDI oligonucleotide to inhibit DNA synthesis. Thus, the present invention includes a "screening assay" capable of identifying antagonists of the SDI oligonucleotides. Conversely, one may incubate cells in the presence of both an SDI antisense oligonucleotide and a suspected antagonist compound. The cells would be monitored in order to determine whether the compound is able to impair the ability of the antisense oligonucleotide to derepress DNA synthesis. Thus, the present invention includes a "screening assay" capable of identifying antagonists of the antisense oligonucleotides. In a similar manner, agonists of these agents may be alternatively be identified.

Among the agonist compounds which could be identified through the use of such a screening assay are compounds which could be used to induce infertility. Similarly, the assay will permit the identification of compounds capable of either suppressing or inducing tissue regeneration of vascularization. Such compounds may be useful in the treatment of cancer.

In addition to their use in expressing proteins and polypeptides, and in defining desirable analogs, the SDI nucleic acid molecules of the present invention can be used to produce antisense nucleic acid molecules capable of binding to an SDI nucleic acid molecule and inhibiting its activity, etc. A particularly preferred such agent is antisense oligonucleotide.

In general, an "antisense oligonucleotide" is a nucleic acid (either DNA or RNA) whose sequence is complementary to the sequence of a target mRNA molecule (or its corresponding gene) such that it is capable of binding to, or hybridizing with, the mRNA molecule (or the gene), and thereby impairing (i.e. attenuating or preventing) the translation of the mRNA molecule into a gene product. To act as an antisense oligonucleotide, the nucleic acid molecule must be capable of binding to or hybridizing with that portion of target mRNA molecule (or gene) which mediates the translation of the target mRNA. Antisense oligonucleotides are disclosed in European Patent Application Publication Nos. 263,740; 335,451; and 329,882, and in PCT Publication No. WO90/00624, all of which references are incorporated herein by reference.

The present invention is particularly concerned with those antisense oligonucleotides which are capable of binding to or hybridizing with mRNA or cDNA molecules that encode an SDI gene product.

Thus, in one embodiment of this invention, an antisense oligonucleotide that is designed to specifically block translation of an SDI mRNA transcript can be used to de-repress the inhibition of DNA synthesis in a recipient senescent cell.

One manner in which an anti-SDI antisense oligonucleotide may achieve these goals is by having a sequence complementary to that of the translation initiation region of an SDI mRNA and of sufficient length to be able to hybridize to the mRNA transcript of an SDI gene. The size of such an oligomer can be any length that is effective for this purpose. Preferably, the antisense oligonucleotide will be about 10–30 nucleotides in length, most preferably, about 15–24 nucleotides in length.

Alternatively, one may use antisense oligonucleotides that are of a length that is too short to be capable of stably hybridizing to an SDI mRNA under physiologic, in vivo conditions. Such an oligonucleotide may be from about 6–10, or more nucleotides in length. To be used in accordance with the present invention, such an oligonucleotide is preferably modified to permit it to bind to a locus of the translation region of an SDI-encoding mRNA. Examples of such modified molecules include oligonucleotides bound to an antibody (or antibody fragment), or other ligand (such as a divalent crosslinking agent (such as, for example, trimethylpsoralin, 8-methoxypsoralin, etc.) capable of binding to single-stranded SDI mRNA molecules.

An anti-SDI antisense oligonucleotide bound to one reactive group of a divalent crosslinking agent (such as psoralin (for example, trimethylpsoralin, or 8-methoxypsoralin) adduct would be capable of crosslinking to an SDI mRNA upon activation with 350–420 nm UV light. Thus, by regulating the intensity of such light (as by varying the wattage of the UV lamp, by increasing the distance between the cells and the lamp, etc.) one may control the extent of binding between the antisense oligonucleotide and an SDI mRNA of a cell. This, in turn, permits one to control the degree of attenuation of SDI gene expression in a recipient cell.

In general, the antisense oligomer is prepared in accordance with the nucleotide sequence of an SDI gene, and most preferably in accordance with nucleotide sequence of SDI-1 (FIG. 5).

The sequence of the antisense oligonucleotide may contain one or more insertions, substitutions, or deletions of one or more nucleotides provided that the resulting oligonucleotide is capable of binding to or hybridizing with the above-described translation locus of either an SDI mRNA, or cDNA or an SDI gene itself.

Any means known in the art to synthesize the antisense oligonucleotides of the present invention may be used (Zamechik et al., Proc. Natl. Acad. Sci. (U.S.A.) 83:4143 (1986); Goodchild et al., Proc. Natl. Acad. Sci. (U.S.A.) 85:5507 (1988); Wickstrom et al., Proc. Natl. Acad. Sci. (U.S.A.) 85:1028; Holt, J. T. et al., Mol. Cell. Biol. 8:963 (1988); Gerwirtz, A. M. et al., Science 242:1303 (1988); Anfossi, G., et al., Proc. Natl. Acad. Sci. (U.S.A.) 86:3379 (1989); Becker, D., et al., EMBO J. 8:3679 (1989); all of which references are incorporated herein by reference). Automated nucleic acid synthesizer may be employed for this purpose. In addition, desired nucleotides of any sequence can be obtained from any commercial supplier of such custom molecules.

Most preferably, the antisense oligonucleotides of the present invention may be prepared using solid phase "phosphoramidite synthesis." The synthesis is performed with the growing nucleotide chain attached to a solid support derivatized with the nucleotide which will be the 3'-hydroxyl end of the oligonucleotide. The method involves the cyclical synthesis of DNA using monomer units whose 5'-hydroxyl group is blocked (preferably with a 5'-DMT (dimethoxytrityl) group), and whose amino groups are blocked with either a benzoyl group (for the amino groups of cytosine and adenosine) or an isobutyryl group (to protect guanosine). Methods for producing such derivatives are well known in the art.

The antisense and other inhibitor molecules of the present invention may be used to immortalize valuable cell types (such as primary tissue culture cells, etc.) which would otherwise have a transient period of proliferative viability. They may thus be used for research or to permit or facilitate the accumulation of large numbers of cells, as for organ or tissue grafts or transplants. In one embodiment, therefore, the agents of the present invention may be used in conjunction with methods for organ or tissue culture to facilitate such methods.

A use is said to be therapeutic if it alters a physiologic condition. A non-therapeutic use is one which alters the appearance of a user.

The agents of the present invention may be used topically or systemically for a therapeutic or non-therapeutic purpose, such as, for example, to counter the effects of aging, for example on skin tone, color, texture, etc., or on the degeneration of cells, tissue or organs, such as lymphocytes, vascular tissue (such as arteries, arterioles, capillaries, veins, etc.), liver, kidney, heart and other muscle, bone, spleen, etc. The agents of the present invention may be employed to rejuvenate such cells, tissue or organs. Thus, they may be used in pharmaceuticals, and the like, which may comprise, for example, an antisense oligonucleotide, or its equivalent, and a lipophyllic carrier or adjunct, preferably dissolved in a appropriate solvent. Such a solvent may be, for example, a water-ethanol mixture (containing 10% or 30% v/v or more ethanol. Such preparations many contain 000.1% to 1.0% of the antisense oligonucleotide. Suitable carriers, adjuncts and solvents are described in Remington's Pharmaceutical Sciences (16th ed. Osol, A., Ed., Mack, Easton Pa. (1980), which reference is incorporated herein by reference).

Since the antisense and other inhibitor molecules of the present invention are capable of stimulating cellular proliferation, they may be used to promote would healing, recovery from burns, or after surgery, or to restore atrophied tissue, etc. For such an embodiment, these agents may be formulated with antibiotics, anti-fungal agents, or the like, for topical or systemic administration.

Such antisense and other inhibitor molecules of the present invention may be used to stimulate the proliferation of spermatocytes, or the maturation of oocytes in humans or animals. Thus, the agents of the present invention may be used to increase the fertility of a recipient.

The molecules of the present invention may be used to provide gene therapy for recipient patients. In one embodiment, cells or tissue from a patient may be removed from the patient and treated with a molecule of the present invention under conditions sufficient to permit a restoration of an active growing state. In one preferred embodiment of this use, lymphocytes of an individual (such as, for example, an immune compromised individual, such as an AIDS patient, etc., or an immune-competent individual who will serve as a donor of lymphocytes) can be removed and treated with antisense SDI nucleic acids. The administration of these molecules will derepress the lymphocytes. After administration, the lymphocytes are reintroduced into the patient, and have an enhanced ability to combat infection.

The molecules of the present invention are particularly suitable for use in the creation and/or study of animal models for disease or tissue degeneration. Thus, the molecules of the present invention can be used to study effectors of an animal model that is characterized by abnormal aging or cellular degeneration. Similarly, the administration of the SDI molecules (linked, for example to suitable regulatory sequences in order to permit their expression in a recipient cell) can be used to create animal models of aging and of tissue degeneration.

IV. Methods of Administration

The agents of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in Remington's Pharmaceutical Sciences (16th ed., Osol. A., Ed., Mack, Easton Pa. (1980)). In order to form a pharmaceutically acceptable composition suitable for effective administration, such compositions will contain an effective amount of an antisense oligonucleotide, or its equivalent, or their functional derivatives, together with a suitable amount of carrier vehicle.

Additional pharmaceutical methods may be employed to control the duration of action. Control release preparations may be achieved through the use of polymers to complex or absorb an antisense oligonucleotide, or its equivalent, or their functional derivatives. The controlled delivery may be exercised by selecting appropriate macromolecules (for example polyesters, polyamino acids, polyvinyl, pyrrolidone, ethylenevinylacetate, methylcellulose, carboxymethylcellulose, or protamine, sulfate) and the concentration of macromolecules as well as the methods of incorporation in order to control release. Another possible method to control the duration of action by controlled release preparations is to incorporate an antisense oligonucleotide, or its equivalent, or their functional derivatives, into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin microspheres, microemulsions, nanoparticles, and nanocapsules or macroemulsions. Such techniques are disclosed in Remington's Pharmaceutical Sciences (1980).

The compositions of the present invention can also be formulated for administration parenterally by injection, rapid infusion, nasopharyngeal absorption (intranasopharangeally), dermoabsorption, or orally. The compositions may alternatively be administered intramuscularly, or intravenously. Compositions for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers, adjuncts or occlusive dressings can be used to increase tissue permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include wetting agents, emulsifying and suspending agents, or sweetening, flavoring, coloring or perfuming agents.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

Generally, the dosage needed to provide an effective amount of the composition will vary depending upon such factors as the recipient's age, condition, sex, and extent of disease, if any, and other variables which can be adjusted by one of ordinary skill in the art.

Effective amounts of the compositions of the invention can vary from 0.01–1,000 mg/ml per dose or application, although lesser or greater amounts can be used.

Having now generally described the invention, the same will be more readily understood through reference to the following examples which are provided by way of illustration, and are not intended to be limiting of the present invention, unless specified.

EXAMPLE 1

CREATION OF THE cDNA LIBRARY

A cDNA library was obtained using RNA from normal human neonatal foreskin fibroblasts, such as the cell line HCA2. To do this, the cells were grown in minimal essential medium with either Earle's or Hanks' balanced salt solution supplemented with 10% fetal bovine serum (GIBCO or Hyclone). Cells were cultured, and their in vitro life span was determined, under the conditions disclosed by Smith, J. R., and Braunschweiger, K. I., *J. Cell Physiol.* 98:597–601

(1979), hereby incorporated by reference. Quiescent cells were made by replacing the normal culture medium with culture medium containing 0.5% serum before the cells become confluent. The cells were maintained in low serum culture for up to 3 weeks.

Total cellular RNA was isolated either by the guanidium thiocyanate/CsCl method (Garger, S. J. et al., *Biochem. Biophys. Res. Commun.* 117:835–842 (1983)) or a guanidium thiocyanate/phenol method (Chomczynski, P., and Sacchi, N., *Anal. Biochem.* 162:156–159 (1987), RNAzol B. Biotecz Lab. Inc. TX). Poly A+ RNA was isolated by oligo (dT) cellulose column chromatography (Collaborative Res. MA).

10 µg of the poly A+ RNA derived from senescent cells, as described above, was converted to double stranded cDNAs by using RNase H⁻MMLV reverse transcriptase according to the instructions of the supplier (BRL, MAD), and blunt-ended by T4 polymerase treatment. The double stranded cDNA preparations were size fractionated by agarose gel electrophoresis, and the 2–4.5 kb fraction isolated, for insertion into an expression vector.

The expression vector used for this purpose was a 3.4 kb plasmid, designated pcDSRαΔ (FIG. 1). Plasmid pcDSRαΔ is a derivative of the plasmid pcDSRα296, which includes the Okayama-Berg SV40 promoter and the LTR from HTLV-1 (Takebe, Y. et al., *Mol. Cell. Biol.* 8:466–472 (1988); provided by Dr. M. Yoshida (Cancer Inst. of Japan)). Plasmid pcDSRαΔ was formed by removing a 336 base pair (bp) segment of the PstI-KpnI fragment of pcDSRα296 and replacing it with 28 bp of a PstI-KpnI fragment from pUC19. The resulting plasmid (pcDSRαΔ) was used as a cloning and expression vector.

Plasmid pSV2cat (Gorman, C. et al., *Mol. Cell. Biol.* 2:1044–1051 (1982)) was provided by Dr. Gretchen Darlington (Texas Children's Hospital). The pcD vector (Okayama, H., and Berg. P., *Mol. Cell. Biol.* 3:280–289 (1983)) was provided by Dr. H. Okayama (Osaka University, Japan); the plasmid has the chloramphenicol acetyltransferase ("CAT") gene inserted between the SV' promoter and SV40 poly A signal. pcDRαΔ-cat was constructed from pcDSRαΔ by the insertion of 0.8 Kb of a HindIII-SmaI digested SRα promoter fragment into HindIII digested pSVOcat via a two step ligation. A very strong promoter was desired in order to allow for efficient expression screening of the cDNA library. From an analysis of several mammalian expression vectors (pSV2cat, pcD-cat and pcDSRαΔ-cat, transfected into young cells), the SRα promoter was found to drive the expression of the CAT gene at high efficiency in young cycling cells. The relative CAT activities of these plasmids were calculated by normalizing to the amount of protein used for each reaction. The transcriptional efficiency was about 20-fold greater than that of the conventional pSV2 promoter, which utilizes the SV40 early gene promoter.

pCMVβ carries the *E. coli* β-galactosidase gene driven by the human cytomegalovirus immediate early gene promoter (MacGregor, G. R., and Caskey, C. T., *Nucleic Acids Res.* 17:2365 (1989); provided by Dr. Grant MacGregor, Baylor College of Medicine, TX). Plasmid Pβ440, which carries 443 bp of the human β-actin sequence (Nakajima-Iijima, S. et al., *Proc. Natl. Acad. Sci.* 82:6133–6137 (1985); provided by Dr. Kozo Makino, Osaka University, Japan). Plasmid pHcGAP (Tso, J. Y. et al., *Nucleic Acids Res.* 13:2485–2502 (1985)), which carries a full length human glyceraldehyde 3 phosphate dehydrogenase (GAPDH) cDNA, was obtained from the American Type Culture, Collection, Rockville, Md.

For cDNA antisense expression, full length cDNA fragments were excised by BamHI digestion from the originally cloned pcDSRαΔ vector, and re-ligated in the reverse direction.

cDNAs recovered from the agarose gel were directly inserted into a calf intestine alkaline phosphatase treated SmaI site of pcDSRαΔ, and transformed into *E. coli* MC1061 or DH-1. Ampicillin resistance colonies were picked randomly and plasmid sizes determined. These procedures were repeated until 2–4.5 kb cDNA insertions were achieved in more than 90 percent of the plasmids tested. Then each *E. coli* colony was picked with toothpicks and 5 colonies combined into one cDNA pool. More than 400 cDNA pools were prepared, grown in 96 well microtiter plates and stored in 14% glycerol at −70° C. For DNA isolation, *E. coli* from each cDNA pool was cultured in 200 ml, and treated by the standard methods of ethydium bromide/CsCl ultracentrifugation (Garger, S. J. et al., *Biochem Biophys. Res. Commun.* 177:835–842 (1983)) one or two times, followed by dialysis against E (10 mM Tris pH 8.0, 1 mM EDTA) solution.

EXAMPLE 2

DEAE-DEXTRAN MEDIATED TRANSFECTION AND TRANSIENT EXPRESSION SCREENING

Young, cycling fibroblast cells were seeded at a density of 0.9–1.2×10$^5$ per well in 6 well tissue culture plates or 35 mm tissue culture dishes 18 h prior to transfection. Transfection was done as described by Cullen, B. R., In: *Guide to Molecular Cloning Techniques, Methods in Enzymology.*, S. L. Berger and A. R. Kimmel (ed.) Academic Press, pp. 684–704 (1987); herein incorporated by reference with minor modifications as described below.

For each transfection, 100 ng of pCMVβ and 400 ng of a cDNA pool were mixed and suspended in 190 µl of phosphate buffered saline (PBS) solution and 10 µl of 10 mg/ml of DEAE-dextran (Pharmacia, MW ⁻500,000) was added. 400 ng of the cloning vector plasmid, pcDSRαΔ, was used with pCMVβ as a control. After washing the cells with PBS once, DNA solutions were added and the cells incubated for up to 45 min at 37° C. in a CO$_2$ incubator. Then 2 ml of cell culture medium with serum, containing 64 µM chloroquine (Sigma, Mo.) was added directly and incubated for another 2.5 h. After the chloroquine treatment, the transfection mixture was removed and the cells treated with 10% dimethyl sulfoxide in cell culture medium with serum for 2 min. Cells were then returned to fresh cell culture medium with serum and incubated to allow for expression of the transfected DNA.

18 h after transfection, 0.5 µCi/ml of $^3$H-thymidine was added and the incubation continued for another 48 h. Cells were fixed by adding by 25 µl of 25% of glutaraldehyde solution to the culture medium and incubated for 5 min at room temperature, followed by three washings with PBS. Immediately after washing, cells were treated with the X-gal reaction mixture (1mM MgCl$_2$, 3 mM K$_4$[Fe(CN)$_6$], 3 mM K$_3$[Fe(CN)$_6$], 0.1% triton X-100, and 1 mM X-gal dissolved in 0.1M sodium phosphate buffer (ph 7.5) containing 10 mM KCl) for up to 20 min to allow light-blue staining of the cells. After the X-gal staining, the cells were washed with water, dried and processed for autoradiography using Kodak NTB nuclear track emulsion (Kodak, N.Y.). DNA synthesis activity in X-gal positive cells was then determined. The percent inhibition of DNA synthesis was calculated using the formula:

$$\frac{\begin{array}{c}\text{\% labeled nuclei in} \\ \text{blue cells in which} \\ \text{control plasmids} \\ \text{were transfected}\end{array} - \begin{array}{c}\text{\% labeled nuclei in} \\ \text{blue cells in which} \\ \text{cDMA plasmids} \\ \text{were transfected}\end{array}}{\begin{array}{c}\text{\% labeled nuclei in blue cells in which} \\ \text{control plasmids were transfected}\end{array}} \times 100$$

Candidate cDNA pools were divided into individual cDNAs and screened further for the identification of specific DNA synthesis inhibitory cDNA sequences.

Nuclear microinjection of young cycling cells was preferred as described by (Lumpkin, C. K. et al., *Mol. Cell Biol.* 6:2990–2993 (1986), herein incorporated by reference). Briefly, 5,000–10,000 cells were plated onto 22 mm square etched grid coverslips (Bellco) in 35 mm tissue culture dishes. Three or four days later, nuclear microinjections were performed on a minimum of 300 cells, using either pCMVβ+cDNA plasmid or pCMBβ+pcDSRαΔ (which served as the control). Plasmids were co-microinjected at a concentration of 50 ng/µl each. 18 hours after microinjection, the cells were labeled with $^3$H-thymidine for 24 h, fixed, stained with X-gal and processed for autoradiography. The present inhibition of DNA synthesis was calculated as above.

Northern blot analysis was performed using either 5 µg of total RNA or 1 µg poly A+ RNA. The RNA was size fractionated by electrophoresis on formaldehyde-agarose gels and transferred to nylon membranes (ICN; Biotrans, formerly Pall Biodyne A) as described by Maniatis, T. et al., Molecular cloning: A Laboratory Manual; Cold Spring Harbor Laboratory, Cold Spring Harbor, N.Y. (1982), herein incorporated by reference. Radioactive probes were prepared by the random primer method, and blots hybridized as described by Maniatis, T. et al., Molecular cloning: A Laboratory Manual; Cold Spring Harbor Laboratory, Cold Spring Harbor, N.Y. (1982).

The northern blot analyses revealed that the sizes of the cellular transcripts of the SDIs were compatible with the sizes of the SDI cDNAs. This was expected since successful expression screening requires full-length cDNA insertions into the vector.

For rehybridization with β-actin or glyceraldehyde phosphate dehydrogenase (GAPDH) probe, filters were repeatedly stripped of the labelled probes following the manufacturer's instructions. The data were quantitated by Ambis Radioanalytic Scanning System.

An assay or CAT activity was determined as follows: Young cycling cells were seeded into 35 mm dishes and 500 ng of plasmid transfected as described above. 24 h after the transfection, the cells were scraped from the dish, and CAT assay performed as described by Gorman (Gorman, C., In: DNA Cloning, A Practical Approach. IRL Press, Oxford, England, pp. 143–164 (1985), herein incorporated by reference).

EXAMPLE 3

CDNA CLONING OF THE SENESCENT CELL DERIVED INHIBITORS (SDI) OF DNA SYNTHESIS

Double stranded cDNAs were synthesized from senescent cell derived poly A+ RNA, which as been shown to inhibit DNA synthesis in young cells when microinjected into the cytoplasm (Lumpkin, C. K. et al., *Science* 232:393–395 (1986)). The cDNAs were size fractionated, inserted into pcDSRαΔ. The resulting *E. coli* clones were dived into small pools. Plasmids from each pool were co-transfected with the transfection maker plasmid, pCMBVβ, which allowed a determination of the labelling index of transfected cells specifically, since even in high efficiency transfection, frequencies varied from experiment to experiment. Transfection frequencies of the marker plasmid ranged from 30–90%. About 200 cDNA pools were screened and four pools remained positive for DNA synthesis inhibitory activity after five repeated transfections. The candidate pools were then divided into individual plasmids and screened further.

Three independent positive plasmid clones were obtained. In the cDNA pool A, only one plasmid, No. 2, exhibited strong DNA synthesis inhibitory activity. Similarly, in pools B and C only one cDNA clone caused inhibition. The size of inserted cDNAs was 2:1 kb, 1.2 kb and 2.7 kb, respectively, These cDNA sequences have been designated as senescent cell derived inhibitors, SDI-1, SDI-2 and SDI-3, respectively.

The nucleotide sequence of the SDI-1 cDNA clone (SEQ ID NO: 1), and the amino acid sequence of SDI-1 (SEQ ID NO: 2) have been determined. The cDNA sequence presented herein for SDI-1 differs from that described in U.S. patent application Ser. No. 07/808,523, now abandoned, in possessing an unrecited G at position 286, and in having the sequence CG rather than GC at position 1843–1844. The presently disclosed sequence was obtained through the re-sequencing of the pcDSRαΔ-SDI-1 plasmid whose isolation and characteristics were described in U.S. patent application Ser. No. 07/808,523, now abandoned. *E. coli* DH5 transformed with the pcDSRαΔ-SDI-1 plasmid was deposited with the American Type Culture Collection, Rockville, Md. USA, on Oct. 1, 1992, and has been accorded accession number ATCC 69081.

EXAMPLE 4

MICROINJECTION OF SDI SEQUENCES INTO YOUNG CYCLING CELLS

In order to verify the functional activity of SDI sequences, microinjections were performed. A plasmid carrying either SDI-1 or SDI-2 was co-microinjected with the marker plasmid into the nuclei of young cycling cells. The labelling index of the resulting blue cells was determined (Table 1). These plasmids showed strong inhibitory activity on DNA synthesis of young cells. For control experiments, the empty vector was co-microinjected with the marker plasmid. This caused slight inhibition when the labelling index was compared with uninjected cells, a phenomenon also observed in transfection experiments. Microinjections with SDI-3 were not performed because the inhibitory activity was lower than SD-1 and SD-2 transfection experiments.

TABLE 1

Microinjection of Various Plasmids Into Young Cycling Cells

| | Plasmids Injected | No. of Cells Injected | No. of Labelled Nuclei Per Total Blue Cells* | Labelling Index (%) | % Inhibition |
|---|---|---|---|---|---|
| Exp. 1 | pCMVβ + pcDSRαΔ† | 335 | 58/97 | 59.8 | 0 |
| | pCMVβ + SDI-1 | 380 | 20/89 | 22.5 | 62.4 |
| | pCMVβ + | 380 | 6/82 | 7.3 | 87.8 |

TABLE 1-continued

Microinjection of Various Plasmids Into Young Cycling Cells

|  | Plasmids Injected | No. of Cells Injected | No. of Labelled Nuclei Per Total Blue Cells* | Labelling Index (%) | % Inhibition |
|---|---|---|---|---|---|
| Exp. 2 | SDI-2 pCMVβ + pcDSRαA† | 423 | 68/109 | 62.3 | 0 |
|  | pCMVβ + SDI-1 | 465 | 26/98 | 26.5 | 57.5 |
|  | pCMVβ + SDI-2 | 475 | 27/118 | 22.9 | 63.2 |

†Control
*This is the number of cells expressing detectable levels of β-galactosidase. The concentration of each DNA was 50 μg/ml.

EXAMPLE 5

ANTISENSE DNA TRANSFECTION

Figure 3:
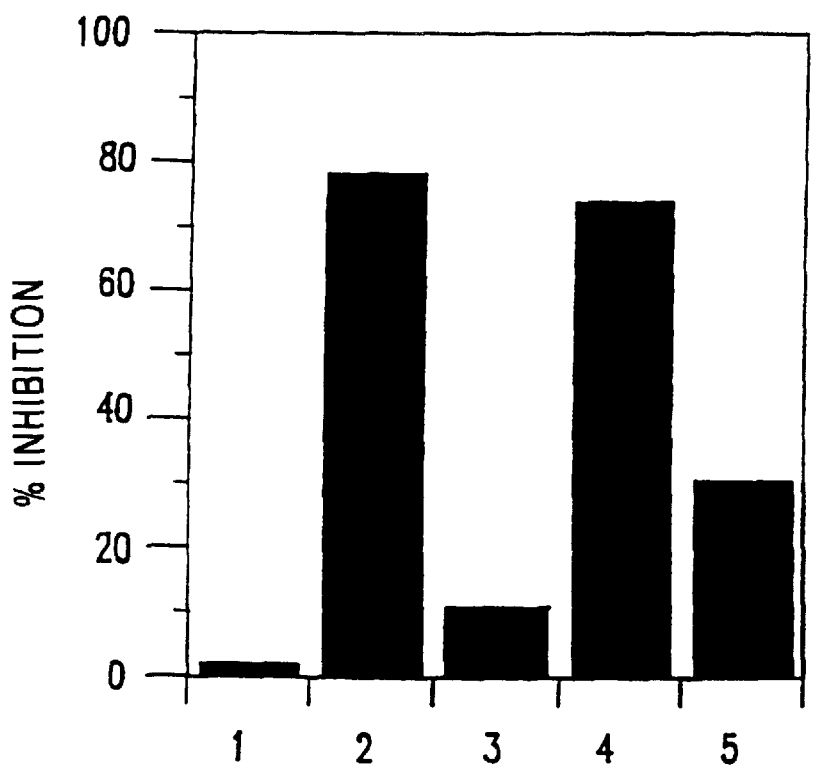
FIG. 3 shows antisense SDI cDNA transfection. Antisense cDNA expression plasmids were made and co-transfected with pCMVβ into young cells. Lane 1: control pcdSRαΔ, lane 2: pcDSRαΔ-SDI-1, lane 3: pcDSRαΔ antiSDI-1, lane 4: pcDSRαΔ-SDI-2, lane 5: pcDSRαΔ-antiSDI-2.

In order to examine whether any inhibitory activities are sequence orientation specific, antisense expression vectors of SDI-1 and SDI-2 sequences were constructed. Since both sequences lacked BamHI sites and since BamHI sites were present at both ends of the cDNA (FIG. 1), the sequences were easily excised and religated in the opposite orientation. Transfection of antisense sequences resulted in no inhibition of DNA synthesis in young cells (FIG. 3). In addition, no enhancement was observed. The results clearly indicate the sequence orientation specificity of the SDI activity, and suggest the presence of specific gene products coded by the cDNA sequences.

EXAMPLE 6

EXPRESSION OF SDI mRNAS DURING CELLULAR SENESCENCE

To examine the changes in SDI mRNA expression during cellular senescence, total RNA from young and senescent cells was hybridized to 32P-labelled SDI cDNA probes. The SDI-1 probe hybridized to a 2.1 kb cellular transcript, SDI-2 hybridized to a 1.4 kb transcript, and SDI-3 hybridized to a 2.5 kb transcript (Table 2). Table 2 provides a quantitation of the total RNA northern analysis of expression of SDI genes in young (Y) and senescent (S) cells. 5 μg each of total RNA from young and senescent cells were hybridized with SDI probes. The filters were repeatedly stripped of the radioactive probe and rehybridized with the probes for the internal controls. The relative amount of SDI mRNA in each sample was normalized by the amount of GAPDH detected on the same filter and by the relative amount of SDI/GAPDH.

TABLE 2

Quantitation of the Northern Analysis

|  | SDI-1 | | SDI-2 | | SDI-3 | |
|---|---|---|---|---|---|---|
| ATTRIBUTE | Y | S | Y | S | Y | S |
| Relative Amount of SDI | 1.0 | 3.3 | 1.0 | 0.31 | 1.0 | 0.31 |
| Relative Amount ot GAPDH | 1.0 | 0.37 | 1.0 | 0.36 | 1.0 | 0.38 |
| Relative Amount of SDI/GAPDH | 1.0 | 9.3 | 1.0 | 0.86 | 1.0 | 0.82 |

During cellular senescence, the SDI-1 message increased about 3-fold, which SDI-2 and SDI-3 messages decreased 3-fold. The same filters were rehybridized with a β-actin, and then to a GAPDH probe as internal controls. The results demonstrated that expression of both control genes decreased about 3-fold during cellular senescence. In previous studies, a 2–3 fold decrease of β-actin expression during cellular senescence had been observed (Kumazaki, T. et al., *Exp. Cell Res.* 195:13–19 (1991); Seshadri, T., and Campisi, J. *Science* 247:205–209 (1990); Furth, J. J. *J. Gerontol.* 46:B122–124 (1991). The decreased expression of both β-actin and GAPDH genes in senescent cells led to the use of poly A+ RNA for northern analysis. Poly A+ RNA was isolated from the total cellular RNA preparations used for Table 2, and hybridized to SDI cDNA, followed by probing with β-actin and GAPDH respectively (Table 3). Table 3 discloses the results of a poly A+ RNA Northern analysis of SDI gene expression in young (Y) and senescent (S) cells. 1 μg each of poly A+ RNA from young and senescent cells were used for the analyses. The relative amount of SDI mRNA in each sample was calculated as in Table 2.

TABLE 3

Quantitation of the Northern Analysis

|  | SDI-1 | | SDI-2 | | SDI-3 | |
|---|---|---|---|---|---|---|
| ATTRIBUTE | Y | S | Y | S | Y | S |
| Relative Amount ot GAPDH | 1.0 | 0.83 | 1.0 | 0.87 | 1.0 | 0.87 |
| Relative Amount of SDI/GAPDH | 1.0 | 11.4 | 1.0 | 1.0 | 1.0 | 1.0 |

The results clearly indicated that the expression of both β-actin and GAPDH was equal in young and senescent cells when they were compared on the basis of mRNA, consistent with previous observations. When SDI gene expression was compared at the mRNA level, SDI-1 mRNA was increased 11-fold in senescent cells, whereas expression of SDI-2 and SDI-3 remained constant throughout the in vitro lifespan (Table 3). This result suggests that SDI-1 is a senescent cell specific inhibitor of DNA synthesis, whereas SDI-2 and SDI-3 are most likely more general inhibitors involved in cell cycle regulation.

EXAMPLE 7

CHANGES OF POLY A RNA CONTENT DURING CELLULAR SENESCENCE

The observation that the results of the total versus poly A+ RNA northern analyses were quantitatively different, indicated that the poly A+ RNA content in total RNA preparations might change during cellular senescence. To test this hypothesis, cells were cultivated serially and total RNA was harvested at different population doubling levels. Poly A+ RNA was isolated from each sample.

Figure 4:
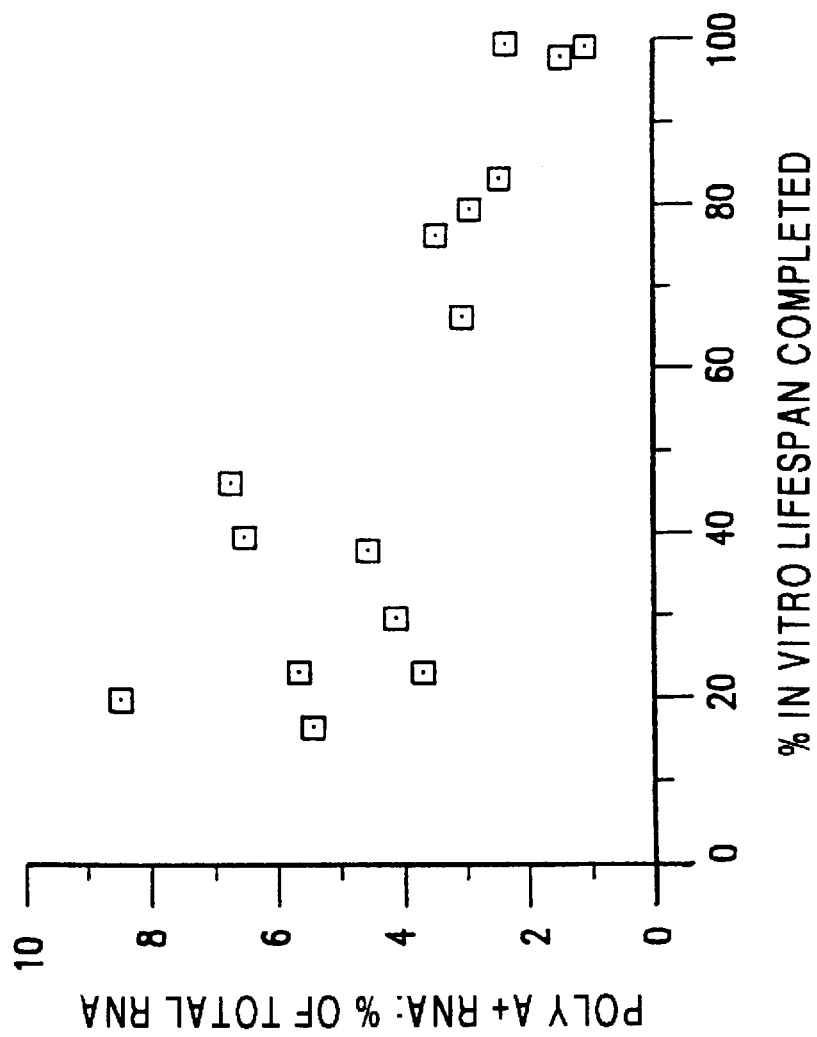
FIG. 4 shows the changes in poly A+ RNA recovery from total RNA during cellular aging.

The result clearly indicated that poly A+ RNA content decreased gradually during cellular senescence (FIG. 4). In FIG. 4, cells were cultivated serially and totally RNA was harvested. Poly A+ RNA: % of total RNA was plotted against the culture's age (% in vitro life span completed). Senescent cells had 3–4 fold less poly A+ RNA when compared with very young cells. However, when total RNA content per cell was calculated, senescent cells had 1.3–1.5 fold more than young cells, (see, Cristofalo, V. J., and Kritchevsky, D., *Med. Exp.* 19:313–320 (1969)).

In order to determine whether SDI-1 message increased gradually during subcultivation or whether a rapid increase occurred near the end of the in vitro life span, poly A+ RNA from cultures at different population doublings was hybridized with the $^{32}$P labelled SDI-1 probe. This analysis revealed that SDI-1 expression increased as the cultures became senescent, with a major change occurring during the final few passages (Table 4). Table 4 shows the accumulation of SDI-1 mRNA during cellular aging process. 1 µg each of poly A+ RNA from the cells of different population doublings were hybridized to SDI-1 probe. The relative amount if SDI-1 mRNA in each sample was calculated as in Table 2.

TABLE 4

Quantitation of % Lifespan Completed

| ATTRIBUTE | 24% | 37% | 46% | 66% | 78% | 88% | 100% |
|---|---|---|---|---|---|---|---|
| Relative Amount of GAPDH | 1.0 | 1.6 | 1.5 | 1.3 | 1.4 | 1.3 | 0.9 |
| Relative Amount of SDI/GAPDH | 1.0 | 2.2 | 2.1 | 4.0 | 3.5 | 6.2 | 20.5 |

Changes in SDI-1 expression during quiescence were also examined. Young, quiescent cells were maintained in 0.5% fetal bovine serum (FBS)-containing medium for up to three weeks. Total RNA was harvested each week and the amount of RNA hybridizing to the SDI-1 probe was analyzed. SDI-1 message increased significantly during cellular quiescence (Table 5). Table 5 shows the accumulation of SDI-1 mRNA during cellular quiescence. 4 µg each of total RNA was obtained from the young cells cultured with 0.5% FBS containing medium for 1, 2, 3 weeks, was hybridized with SDI-1 probe. The relative amount of SDI-1 mRNA was calculated as in Table 2 (C: control culture with 10% FBS medium). When the result was normalized to GAPDH expression, SDI-1 expression was found to have increased 18 fold after two weeks in low serum medium compared to that of a control dividing culture in 10% FBS medium.

TABLE 5

Accumulation of SDI-1 mRNA During Cellular Quiescence

| ATTRIBUTE | C | 1 wk | 2 wk | 3 wk |
|---|---|---|---|---|
| Relative Amount of GAPDH | 1.0 | 0.72 | 0.88 | 0.37 |
| Relative Amount of SDI/GAPDH | 1.0 | 12.2 | 18.4 | 14.9 |

The fact that the cellular representation of mRNA vs total RNA was found to change during cellular senescence is significant. During the in vitro aging process, the content of mRNA was to decrease gradually (FIG. 4), in spite of the slight increase of the total RNA per cell. This phenomenon indicates that a gradual decline of the overall gene expressions during the cellular aging process, and explains the decreased expression of β-actin and GAPDH genes in senescent cells when Northern blot analysis was done with total RNA (Table 2). However, the expression levels of these housekeeping genes between young and senescent cells were almost constant when the Northern blot analysis was done with poly A+ RNAs (Table 3). This analysis revealed the strong expression of SDI-1 message in senescent cells, and unchanging expression of SDI-2 and 3 genes throughout the in vitro life span.

EXAMPLE 8

THE SDI-1 gene

The SDI-1 gene codes for a senescent cell specific inhibitor of DNA synthesis. Increased expression of this gene occurred when the cells entered their final few divisions (Table 4). The expression kinetics correlated well with the phenotypic expression of senescence cells. SDI-1 gene expression was also found to increase after young cells were made quiescent and nondividing by serum deprivation (Table 5). This result demonstrates the involvement of this gene in the inhibition of DNA synthesis of cellular quiescence as well as senescence. Cells made quiescent by deprivation of serum growth factors have been shown to produce an inhibitor of DNA synthesis with characteristics similar to the inhibitor from senescent cells (Pereira-Smith, O. M. et al., *Exp. Cell Res.* 160:297–306 (1985); Stein, G. H., and Atkins, L., *Proc. Natl. Acad. Sci. USA.* 83:9030–9034 (1986)).

The fact that SDI-1 expression increases during both senescence and quiescence indicates that it is an inhibitor of DNA synthesis (Smith, J. R., *J. Gerontol.* 45:B32–35 (1990); herein incorporated by reference). Alternatively, SDI-1 sequences might be related to the growth arrest-specific genes recently cloned from mouse cells (Schneider, C. et al., *Cell* 54:787–793 (1988); Manfioletti, G. et al., *Mol. Cell. Biol.* 10:2924–2930 (1990)).

EXAMPLE 9

THE EXPRESSION OF THE SDI-1 GENE PRODUCT

SDI-1 cDNA has been expressed in two different bacterial expression systems, has been transcribed in vitro and translated in two different in vitro systems. Two bacterial expression systems were used in order to maximize the probability of obtaining sufficient amounts of SDI-1 protein. In the first expression system SDI-1 protein was expressed as a glutathione S-transferase fusion protein at yields of 5–10 µg per liter of bacterial culture. The recombinant protein could be cleaved with thrombin and purified in order to give an SDI-1 protein with a few extra amino acids. In the second expression system, a 6 histidine amino terminal tag was utilized in order to aid in purification. This recombinant protein may be used without further modification. Both systems permitted the isolation of pure preparations of protein.

In the course of this experiment, in vitro transcription and translation systems were used to confirm the open reading frame deduced from the nucleic acid sequence of the SDI-1 cDNA. The calculated molecular weight of the SDI-1 protein is approximately 16,000 daltons. The in vitro synthesized protein migrates, by SDS PAGE, with a relative mobility of approximately 21,000 daltons. This small difference may be due to a slightly unusual charge or conformation of the SDI-1 protein. A partial amino acid sequence of the bacterially expressed protein verified the open reading frame (SEQ ID NO:2).

The bacterially expressed proteins were used to generate polyclonal antisera and monoclonal antibodies to the intact native protein. Such antibodies may be more effective in immunoprecipitation of SDI-1 protein and SDI-1 protein complexes than the antisera produced from snythetic peptides. Preliminary immunocytochemical studies, using an antisera of highest affinity antisera #55) which reacted strongly with the fusion protein on a western transfer at a 1:20,000 dilution, suggested that the SDI-1 protein was relatively abundant in senescent cells compared to dividing young cells. In senescent cells the location appears to be perinuclear, whereas in young cells there appears to be a small amount of SDI-1 protein located in the nucleus. In order to obtain specific staining it was necessary to preabsorb the antisera against a fixed cell monolayer of cells which do not express detectable levels of SDI-1 mRNA (TE85). The cells were fixed with 4% paraformaldehyde followed by methanol.

In order to study the cellular phenotype resulting from the induced expression of SDI-1 mRNA in cells which normally express the gene at low levels and to examine the effect of antisense SDI-1 constructs it is desirable to obtain cell lines in which the SDI-1 gene is stably integrated under the control of an inducible promoter. Toward this goal, a functional vector containing SDI-1 under the control of the metallothionine promoter was constructed. Following transfection of this construct into young proliferation competent cells and incubation in the presence of 100 $\mu$M zinc chloride and 2 $\mu$M cadmium chloride, initiation of DNA synthesis was inhibited by about 50%. In the absence of metals there was no inhibition of DNA synthesis. The inhibitory activity observed is not due to metal toxicity since cells transfected with the control vector (pcDSR$\alpha$) and grown in the presence of metals were found to have approximately 90% of the DNA snythetic capacity of cells ttransfected with the same plasmid grown in the absence of metals.

In order to demonstrate that the inhibitory effects observed with SDI-1 were not related to the nature of the specific promoter used to drive expression, the capacity of SDI-1, expressed from other promoters, to inhibit DNA synthesis was investigated. Young proliferating human fibroblasts were therefore co-transfected with CMB-$\beta$-gal and CMV-SDI-1. Transfection of cells with CMV-$\beta$-gal had little effect on DNA synthesis while CMV-SDI-1 was even more effective than SDI-1 in the pcDSR$\alpha$ vector in these particular experiments.

The SV40 large T antigen is capable of inducing senescent cells to synthesize DNA. It was therefore of interest to determine whether the inhibitory action of SDI-1 could be overcome by the expression of T antigen. Moreover, it was desirable to determine that the action of SDI-1 was not due to the induction of a general metabolic imbalance in cells. If such were the case, one would not expect large T antigen to antagonize its effect. For these reasons, cells were co-transfected with SDI-1 cDNA and vectors in which T antigen was driven by the CMV promoter. Such co-transfection experiments revealed that the inhibitory activity of SDI-1 was largely abolished by the co-expression of the SV40 large T antigen.

Transient transfection assays were performed using an additional normal human fibroblast cell line (neonatal foreskin cell line (CSC303) and the WI38 immortal cell line in order to determine the generality of the inhibitory effect of SDI-1. In both cases, significant inhibition (40–50%) was observed. Furthermore, SDI-1 was found to inhibit SUSMI (40%) but not an SV40 transformed cell line GM639 or HeLa cells (<20%). The results thus far are consistent with earlier results obtained from heterokaryon experiments in which HeLa cells and cells transformed with SV40 virus were not inhibited by fusion with senescent cells. This provides further evidence that SDI-1 behaves like the inhibitor previously detected in senescent cells.

EXAMPLE 10

SOUTHERN ANANLYSIS OF THE SDI-1 GENE

In order to determine whether the absence or inactivity of SDI-1 was responsible for cellular immortality in any of the four complementation groups for indefinite division, genomic DNA and mRNA was examined from cell lines representative of the four groups. Southern analysis revealed the expected 5 and 10 kb bands after digestion with Eco RI. Therefore, no gross deletions or rearrangements have occurred in the SDI-1 gene in these cell lines. By Northern analysis, it was determined that SDI-1 mRNA was lower or absent in the cell lines that have been assigned to complementation groups B and C. SDI-1 was present at higher levels in cell lines representative of complementation groups A and D. This results suggests that part of the mechanism by which the cell lines may have escaped cellular senescence is through the loss of ability to express sufficient levels of the active SDI-1 gene.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A purified protein being substantially free of natural contaminants and capable of inhibiting DNA synthesis in a recipient cell, said protein being senescent cell derived inhibitor-1, SDI-1, and consisting of the amino acid sequence of SEQ ID. NO:2.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 2106 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO (v i) ORIGINAL SOURCE:
    (A) ORGANISM: HOMO SAPIENS
    (B) CELL TYPE: SENESCENT HUMAN CELLS (v i i) IMMEDIATE SOURCE:
    (A) LIBRARY: Senescent cell derived cDNA library
    (B) CLONE: SDI-1

(x i) SEQUENCE DESCRIPTION: SEQ ID NO: 1:

| | | | | | |
|---|---|---|---|---|---|
| CCTGCCGAAG | TCAGTTCCTT | GTGGAGCCGG | AGCTGGGCGC | GGATTCGCCG | AGGCACCGAG | 60 |
| GCACTCAGAG | GAGGCGCCAT | GTCAGAACCG | GCTGGGGATG | TCCGTCAGAA | CCCATGCGGC | 120 |
| AGCAAGGCCT | GCCCCCGCCT | CTTCGGCCCA | GTGGACAGCG | AGCAGCTGAG | CCGCGACTGT | 180 |
| GATGCGCTAA | TGGCGGGCTG | CATCCAGGAG | GCCCGTGAGC | GATGGAACTT | CGACTTTGTC | 240 |
| ACCCAGACAC | CACTGGAGGG | TGACTTCGCC | TGGGAGCGTG | TGCGGGGCCT | TGGCCTGCCC | 300 |
| AAGCTCTACC | TTCCCACGGG | GCCCCGGCGA | GGCGGGATG  | AGTTGGGAGG | AGGCAGGCGG | 360 |
| CCTGGCACCT | CACCTGCTCT | GCTGCAGGGG | ACAGCAGAGG | AAGACCATGT | GGACCTGTCA | 420 |
| CTGTCTTGTA | CCCTTGTGCC | TCGCTCAGGG | GAGCAGGCTG | AAGGGTCCCC | AGGTGGACCT | 480 |
| GGAGACTCTC | AGGGTCGAAA | ACGGCGGCAG | ACCAGCATGA | CAGATTTCTA | CCACTCCAAA | 540 |
| CGCCGGCTGA | TCTTCTCCAA | GAGGAAGCCC | TAATCCGCCC | ACAGGAAGCC | TGCAGTCCTC | 600 |
| GAAGCGCGAG | GGCCTCAAAG | GCCCGCTCTA | CATCTTCTGC | CTTAGTCTCA | GTTTGTGTGT | 660 |
| CTTAATTATT | ATTTGTGTTT | TAATTTAAAC | ACCTCCTCAT | GTACATACCC | TGGCCGCCCC | 720 |
| CTGCCCCCCA | GCCTCTGGCA | TTAGAATTAT | TTAAACAAAA | ACTAGGCGGT | TGAATGAGAG | 780 |
| GTTCCTAAGA | GTGCTGGGCA | TTTTTATTTT | ATGAAATACT | ATTTAAAGCC | TCCTCATCCC | 840 |
| GTGTTCTCCT | TTTCCTCTCT | CCCGGAGGTT | GGGTGGGCCG | GCTTCATGCC | AGCTACTTCC | 900 |
| TCCTCCCCAC | TTGTCCGCTG | GGTGGTACCC | TCTGGAGGGG | TGTGGCTCCT | TCCCATCGCT | 960 |
| GTCACAGGCG | GTTATGAAAT | TCACCCCCTT | TCCTGGACAC | TCAGACCTGA | ATTCTTTTTC | 1020 |
| ATTTGAGAAG | TAAACAGATG | GCACTTTGAA | GGGGCCTCAC | CGAGTGGGGG | CATCATCAAA | 1080 |
| AACTTTGGAG | TCCCCTCACC | TCCTCTAAGG | TTGGGCAGGG | TGACCCTGAA | GTGAGCACAG | 1140 |
| CCTAGGGCTG | AGCTGGGGAC | CTGGTACCCT | CCTGGCTCTT | GATACCCCCC | TCTGTCTTGT | 1200 |
| GAAGGCAGGG | GGAAGGTGGG | GTCCTGGAGC | AGACCACCCC | GCCTGCCCTC | ATGGCCCCTC | 1260 |
| TGACCTGCAC | TGGGGAGCCC | GTCTCAGTGT | TGAGCCTTTT | CCCTCTTTGG | CTCCCCTGTA | 1320 |
| CCTTTTGAGG | AGCCCCAGCT | ACCCTTCTTC | TCCAGCTGGG | CTCTGCAATT | CCCCTCTGCT | 1380 |
| GCTGTCCCTC | CCCCTTGTCC | TTTCCCTTCA | GTACCCTCTC | AGCTCCAGGT | GGCTCTGAGG | 1440 |
| TGCCTGTCCC | ACCCCCACCC | CCAGCTCAAT | GGACTGGAAG | GGGAAGGGAC | ACACAAGAAG | 1500 |
| AAGGGCACCC | TAGTTCTACC | TCAGGCAGCT | CAAGCAGCGA | CCCCCCCCTC | CTCTAGCTGT | 1560 |
| GGGGGTGAGG | GTCCCATGTG | GTGGCACAGG | CCCCCTTGAG | TGGGGTTATC | TCTGTGTTAG | 1620 |
| GGGTATATGA | TGGGGGAGTA | GATCTTTCTA | GGAGGGAGAC | ACTGGCCCCT | CAAATCGTCC | 1680 |
| AGCGACCTTC | CTCATCCACC | CCATCCCTCC | CCAGTTCATT | GCACTTTGAT | TAGCAGCGGA | 1740 |
| ACAAGGAGTC | AGACATTTTA | AGATGGTGGC | AGTAGAGGCT | ATGGACAGGG | CATGCCACGT | 1800 |
| GGGCTCATAT | GGGGCTGGGA | GTAGTTGTCT | TTCCTGGCAC | TAAGCTTGAG | CCCCTGGAGG | 1860 |
| CACTGAAGTG | CTTAGTGTAC | TTGGAGTATT | GGGGTCTCAC | CCCAAACACC | TTCCAGCTCC | 1920 |
| TGTAACATAC | TGGCCTGGAC | TGTTTTCTCT | CGGCTCCCCA | TGTGTCCTGG | TTCCCGTTTC | 1980 |
| TCCACCTAGA | CTGTAAACCT | CTCGAGGGCA | GGACCACAC  | CCTGTACTGT | TCTGTGTCTT | 2040 |
| TCACAGCTCC | TCCCACAATG | CTGATATACA | GCAGGTGCTC | AATAAACGAT | TCTTAGTGAA | 2100 |

(2) INFORMATION FOR SEQ ID NO: 2:

(i) SEQUENCE CHARACTERISTICS:
        (A) LENGTH: 164 amino acids
        (B) TYPE: amino acid
        (C) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: HOMO SAPIENS
        (B) STRAIN: SDI-1

(vii) IMMEDIATE SOURCE:
        (C) LIBRARY: Senescent cell derived cDNA library (xi) SEQUENCE DESCRIPTION: SEQ ID NO: 2:

```
Met Ser Glu Pro Ala Gly Asp Val Arg Gln Asn Pro Cys Gly Ser Lys
 1               5                  10                  15

Ala Cys Arg Arg Leu Phe Gly Pro Val Asp Ser Glu Gln Leu Ser Arg
            20                  25                  30

Asp Cys Asp Ala Leu Met Ala Gly Cys Ile Gln Glu Ala Arg Glu Arg
        35                  40                  45

Trp Asn Phe Asp Phe Val Thr Glu Thr Pro Leu Glu Gly Asp Phe Ala
    50                  55                  60

Trp Glu Arg Val Arg Gly Leu Gly Leu Pro Lys Leu Tyr Leu Pro Thr
65                  70                  75                  80

Gly Pro Arg Arg Gly Arg Asp Glu Leu Gly Gly Gly Arg Arg Pro Gly
                85                  90                  95

Thr Ser Pro Ala Leu Leu Gln Gly Thr Ala Glu Glu Asp His Val Asp
            100                 105                 110

Leu Ser Leu Ser Cys Thr Leu Val Pro Arg Ser Gly Glu Gln Ala Glu
        115                 120                 125

Gly Ser Pro Gly Gly Pro Gly Asp Ser Gln Gly Arg Lys Arg Arg Gln
    130                 135                 140

Thr Ser Met Thr Asp Phe Tyr His Ser Lys Arg Arg Leu Ile Phe Ser
145                 150                 155                 160

Lys Arg Lys Pro
```